United States Patent [19]

Chang

[11] Patent Number: 4,834,972

[45] Date of Patent: May 30, 1989

[54] GELS OF TELOMER-COPOLYMERS OF ETHYLENE AND A SILANE

[75] Inventor: Irving B. Chang, Morristown, N.J.

[73] Assignee: Allied-Signal Inc., Morristown, N.J.

[21] Appl. No.: 39,893

[22] Filed: Apr. 20, 1987

[51] Int. Cl.⁴ .................. A61K 31/74; C08L 83/00
[52] U.S. Cl. ..................... 424/78; 424/59;
424/63; 524/588
[58] Field of Search ............ 526/279; 424/78, 59,
424/63; 524/588

[56] References Cited

U.S. PATENT DOCUMENTS

| | | | |
|---|---|---|---|
| 4,425,364 | 1/1984 | Vanlerberghe et al. | 424/69 |
| 4,446,283 | 5/1984 | Doi et al. | 526/279 |
| 4,478,853 | 10/1984 | Chaussee | 424/78 |
| 4,574,133 | 3/1986 | Umpleby | 525/370 |
| 4,578,266 | 3/1986 | Tietjen et al. | 424/63 |
| 4,699,780 | 10/1987 | Jennings et al. | 424/63 |

*Primary Examiner*—Joseph L. Schofer
*Assistant Examiner*—Peter F. Kulkosky
*Attorney, Agent, or Firm*—Harold N. Wells; Roger Criss

[57] ABSTRACT

Products for the personal care industry are formulated with gels comprising a telomer-copolymer of ethylene and a silane, and a solvent. Preferably a silicone oil or a substitute is included with sufficient solvent to provide a stable ternary gel. The gels provide the inherent advantages of silicones in such applications while reducing the amount required and improving stability of the formulations.

17 Claims, 7 Drawing Sheets

GELS OF TELOMER-COPOLYMERS OF ETHYLENE AND A SILANE

FIELD OF THE INVENTION

This invention relates generally to compositions useful in the personal care industry. More particularly, it relates to gels which can be used to prepare various compositions for contact with the skin.

BACKGROUND OF THE INVENTION

Products formulated for use in the personal care industry include many ingredients. In recent years, many products have included silicones to obtain certain advantages. The silicones are easy to rub out, softening the skin and providing lubricity, glossy appearance, and smoothness. They also provide a water barrier and are not easily washed away. However, they are not oily or sticky and the film allows the skin to breathe. The silicones provide these advantages while being inert and safe to use. However, they tend to flow from or are easily rubbed off the skin. One method of introducing silicones into personal care products would be to incorporate them in a compatible and stable gel which could be mixed with other ingredients in the formulation of personal care products while the resulting film still retains the excellent properties of the silicone oils. When silicones are added to conventional gelling agents such as vegetable or animal waxes, paraffin, or low molecular weight ethylene vinyl acetate copolymers, the exhibit limited compatibility and often lose the attractive features of the silicone oils.

The present invention relates to new gels found to be useful in personal care formulations which inherently provide the advantages of silicones and represent improvements over gels of the prior art.

SUMMARY OF THE INVENTION

The gels of the invention may be either binary or ternary compositions which include a telomer-copolymer of ethylene and a silane, and a solvent for the polymer. A third component may be added, preferably a silicone oil but a substitute may be used. While the binary compositions are compatible in all proportions, the ternary compositions are not, and it has been found that the amount of solvent must be sufficient to permit a stable gel to be formed.

The telomer copolymers used in gels of the invention are of ethylene and silane monomers which have the formula:

where:
X is 0 or 1
y is 0 or 1
$R^1$ is H or an aliphatic radical having 1-5 carbon atoms
$R^2$ is a saturated aliphatic radical having 1-10 carbon atoms or an aryl radical having no more than two aromatic rings
m is 1-5
n is 1-5
v is 1-3
$R^3$ is H or an aliphatic radical having 1-4 carbon atoms said copolymer having a number average weight of from 500-10,000 and containing from 0.1 to 70% by weight of the silane.

The solvent may be at least one member of the group consisting of fatty alcohols, fatty esters, polybutene, hydrocarbon oils such as mineral oil, and petrolatum, animal-derived oils such as lanolin, lanolin alcohol, squalane, and mink oil or vegetable-derived oils such as jojoba oil, almond oil, and the like.

Ternary compositions may be made with silicone oils such as polydimethyl siloxane, polypheny methyl siloxane, cyclomethicone, and the like. Substitute materials for the silicone oils include such materials as propylene glycol, castor oil, and the like which are familiar to those skilled in the art.

Typical ternary compositions are illustrated in the accompanying FIGS. 1-14 with areas marked in which the compositions produce compatible and stable gels and those areas in which the compositions are unsatisfactory. The figures also show that binary gels which do not contain silicones or substitutes are compatible in all proportions. Preferably, binary gels contain about 8-40 weight percent of the polymer, the remainder being the solvent.

The stable gels of the invention are useful in formulating various products for the personal care industry.

DESCRIPTION OF THE PREFERRED EMBODIMENTS

Telomer-Copolymers of Ethylene and Silanes

The telomer-copolymers used in gels according to the invention are described in co-pending applications Ser. No. 898,826, and Ser. No. 124,371 which are incorporated by reference.

The telomer-copolymers used in gels of the invention are of ethylene and silane comonomers having the formula:

wherein: x is 0 or 1; y is 0 or 1; $R^1$ is H or an aliphatic radical having from 1 to 5 carbon atoms; $R^2$ is a saturated aliphatic radical having from 1 to 10 carbon atoms or an aryl radical having no more than two aromatic rings; m is from 1 to 5; n is from 1 to 5; v is from 1 to 3; $R^3$ is H or an aliphatic radical having from 1 to 4 carbon atoms. $R^1$ is H when x=0.

The copolymers have a number average molecular weight of from 500 to 10,000, preferably from 500 to 5,000, and more preferably from 500 to 3,500. The number average molecular weight is measured by vapor pressure osmometry or gel permeation chromatography. The copolymer contains from 0.1 to 70%, preferably from 0.2 to 50% and more preferably from 0.2 to 30% by weight of the silane comonomer moiety.

$R^1$ is hydrogen or an alkyl radical having from 1 to 5 carbon atoms, such as methyl, ethyl, isopropyl, butyl, tert-butyl, pentyl, and the like.

$R^2$ is an alkyl radical having from 1 to 10 carbon atoms, such as methyl, ethyl, propyl, butyl, tert-butyl, pentyl, hexyl, heptyl, octyl, and decyl, or an aryl such as benzyl or naphthyl.

$R^3$ is hydrogen or an alkyl radical having from 1 to 4 carbon atoms such as methyl, ethyl, propyl, and butyl.

Examples of the vinyltrialkoxysilanes which can be copolymerized with ethylene include vinyltrimethoxysilane, vinyltriethoxysilane, vinyltripropoxysilane, vinyltriisopropoxysilane, vinyltributoxysilane, vinyltripentoxysilane, vinyl-tris(2-methoxyethoxy)silane, vinyl-tris(2-ethoxyethoxy)silane and the like.

Acryloxyalkyltrialkoxyxilanes which can be copolymerized with ethylene to form copolymers of the present invention include gamma-methacryloxypropyltrimethoxysilane, gamma-acryloxypropyltrimethoxysilane, gamma-methacryloxyethyltrimethoxysilane, gamma-methacryloxypropyl-tris(2-methoxyethoxy)silane, gamma-methacryloxypropyltris(2-ethoxyethoxy)silane, and the like.

The copolymers of ethylene and silane comonomers as described above are capped by a telogen to form the telomers. The telogens are chain transfer agents which are a co-reactant material because they react and are consumed by combining in the polymerized material to form a telomerized polymer product. This product is a low molecular weight copolymer.

Telogens useful in the present invention include compounds containing carbon, hydrogen, oxygen, and chlorine and are generally saturated compounds in that such compounds are free of olefinic saturation. Examples of useful telogens include alcohols, aldehydes, ketones, chloroform, carbon tetrachloride, and the like. The preferred telogens contain the structures C—O—H and C—Cl. Compounds which contain at least one CH or $CH_2$ group are generally more reactive than analogous compounds containing carbon combined with hydrogen in the form of only $CH_3$ groups. Compounds, especially preferred, have 2–6 aliphatic carbon atoms, not more than two oxygens, or three chlorine atoms and at least one CH or $CH_2$ group. Suitable compounds include alcohols, e.g., methanol; ethanol; normal and isopropanol; primary, secondary and tertiary butanols; cyclohexanol; diacetone alcohol; also ethers, e.g., dimethyl, diethyl and diisopropyl ethers; also ketones, e.g. acetone; methyl ethyl ketone; isobutyl ketones; cyclohexanone; also esters, e.g., methyl, ethyl, propyl and butyl formates, acetates, propionates butyrates, malonates, orthoformates; acids such as acetic, propionic and butyric acids; and the corresponding acid anhydrides and the corresponding aldehydes; also ethylene oxide; dioxolane; dioxane, methyl, ethyl, propyl, and butyl acetals, lactones; furanes; glycol diacetate, etc.; also toluene, ethylbenzene, cumene, n-propylbenzene, butylbenzenes; amyl benzenes, etc.; also chloroform and carbon tetrachloride. An especially preferred telogen is isopropanol. The amount of telogen as well as the particular agent employed and general reaction conditions are factors influencing the product and the production of homogeneous materials. Hence, it is also generally desirable to maintain a substantially constant concentration of telogen within the reaction zone once equilibrium has been established, preferably varying by no more than ±20%, more preferably by no more than ±10%. The actual amount of the telogen agent may vary widely from between about 2% to 60%, usually about 2% to 40% based on the total weight of the feed to or total charge in the reaction zone, more usually between about 15% to 30% depending on the comonomer, the reaction conditions, and nature of the product desired.

The copolymerization is carried out at a temperature range of from 100° to 300° C., preferably 100° to 280° C. and more preferably from 130° to 220° C. The reaction is carried out at a pressure of from 100 to 700 atmospheres, and preferably from 300 to 500 atmospheres. The process proceeds until from 30 to 80%, and preferably from 50 to 70% of each of the monomers is copolymerized. The average residence time of the reactants in the reactor is from 1 to 400, preferably 20 to 400 minutes, more preferably from 40 to 150 minutes and yet more preferably from 40 to 100 minutes.

The process requires a telogen of the type described above. The telogen preferably is maintained in the vapor phase during the process of the invention and hence the lower boiling materials are preferred. It is, therefore, generally desirable that the telogens have a boiling point below 200° C. at atmospheric pressure, preferably below 150° C. Pressure is a factor having a major influence on the amount of telogen employed. Generally, larger amounts of telogen and lower pressures tend to produce the lower molecular weight products. There is from 0.1 to 50 and preferably 0.3 to 20 times as much telogen by weight as the silane comonomer. Excessive amounts of the telogens tend to dissolve the product in the gas phase and upset the desired equilibrium of the reaction. On the other hand, the smaller amounts of telogen and the higher pressure tend to produce the higher molecular weight products, and to further such imbalance beyond permissible limits will result in products which cannot be effectively recovered and which further may undesirably become cross-linked.

The process employs an initiator of a free radical type. Such materials represent well-known classes of catalytic compounds useful in polymerization reactions and other chemical reactions generally. Among suitable initators are peroxy, perhalo, azo compounds, etc., which are moderately stable at 100° C. or above. Specific examples include hydrogen peroxide, acetyl peroxide, diethyl peroxide, lauroyl peroxide, benzoyl peroxide, cumene hydroperoxide, tertiary butyl hydroperoxide, di-tertiary butyl peroxide, molecular oxygen, acetone oxime, t-butylper-acetate, t-butylperoctoate, 1-cyano-1(t-butyl-azo)cyclohexane, 2-(t-butylazo)isobutyronitritrile, 2-t-butylazo-2-phenylpropane, 2-t-butylazo-2-cyano-butane, etc. Suitable catalyst proportions are from 0.09 to 20%, and preferably about 0.1 to about 10% by weight of the telogen or co-reactant injected into the reactor. More preferably there is from 0.5 to 5% by weight of the catalyst based on the weight of the telogen. The particular initiator employed must decompose non-explosively at the reaction temperatures and concentrations.

Solvents

Certain classes of solvents are not useful in personal care applications and among those which are generally acceptable, there are some which are particularly suitable for preparing gels with ethylene-silane copolymers. Particularly useful as solvents in gels according to the invention include fatty esters, fatty alcohols, polybutene, hydrocarbon oils such as mineral oil and petrolatum, animal-derived oils such as lanolin, lanolin alcohol, squalane, and mink oil, or vegetable-derived oils such as jojoba oil, almond oil, and the like.

In contrast to the two component mixtures of the telomer-copolymer in a solvent, which are all compatible, it will be clear from the examples that only some of the binary mixtures of the telomer-copolymers and silicones are mutually soluble. Therefore, solvents serve to broaden the binary mixtures which can be used.

Silicones and Substitutes Therefor

Silicones have been used in personal care products since they provide a number of desirable characteristics. They are easy to rub out and soften the skin and provide lubricity, a glossy appearance and smoothness, but they are not oily or sticky. They provide a water barrier and are not easily washed away, while they are inert and safe to use. However, the silicones are not entirely compatible when used with conventional gelling agents and tend to lose the attractive features of the silicones.

Not all silicones are suitable for personal care applications. However, certain types of silicones have physical properties which make them useful as previously discussed. Particularly useful materials are polydimethyl siloxane, polyphenyl methyl siloxane and cyclomethicone, all of which are commercially available.

Although the silicones are preferred because of their desirable properties, gels suitable for personal care applications may be made from the telomer-copolymers described above and substitutes, such as propylene glycol, castor oil and the like, as will be seen in the examples.

Gel Preparation

Mixtures of the ingredients are prepared by heating and mixing until the blends appear clear and homogeneous. Generally, temperatures in the range of 70° to 110° C. are required with the particular ingredients used in the examples. Then, the clear mixtures are quickly cooled to ambient temperature while being stirred. Not all of the mixtures tested were judged to be satisfactory. Some did not form a single clear phase and were judged to be incompatible. The uniform gels were classified by particle size as measured by microscopic examination. Those having particles in the range of 0.01 to 1 micron were stable, while those in the range of 5 to 30 microns or more were unsable. Borderline gels had particles in the range of 1 to 5 microns.

In each of the following examples, the three ingredients were heated and mixed in a vessel with mild agitation until a clear homogeneous solution was obtained. The container was indirectly cooled with cold water while agitating with a scraping blade mixer as gel was formed. The size of the gel particles was determined from photomicrographs. The results are presented in ternary diagrams which define the incompatible (i.e., unsatisfactory) region and show the compositions which are useful in preparing stable gels. All of the binary mixtures of the copolymers and solvents produce compatible gels, but the preferred compositions contain about 8–40 wt. percent of the polymer. Not all the ternary compositions are compatible as will be seen, and the mixtures are formulated to provide compatible and stable gels.

Copolymers used were selected from the following group, which illustrates a range of properties.

| Typical Properties | COPOLYMERS* | | | | | | |
|---|---|---|---|---|---|---|---|
| | R762A | R762B | R762C | R762D | R724D | R781B | R784G2 |
| Hardness, dmm 25° | 12.0 | 4.0 | 8.0 | 7.0 | — | 30 | 21 |
| Viscosity, CPS, 140° C. | 630 | 475 | 417 | 292 | — | 385 | 430 |
| Drop Point, °C. | 93.3 | 103.7 | 96.5 | 100.7 | — | — | — |
| Density | 0.899 | 0.918 | 0.908 | 0.912 | — | 0.907 | 0.908 |
| Molecular Weight | | | | | | | |
| MW n (number ave.) | 2498 | 2804 | 2261 | 2071 | — | — | — |
| MW w (weight ave.) | 23805 | 6387 | 14925 | 8735 | — | — | — |
| Dispersity, (MWn/MWw) | 9.2 | 2.3 | 6.6 | 4.2 | — | — | — |
| % Silane monomer (vinyltriethoxy silane) | 6.2 | 7.0 | 7.0 | 7.0 | 20.0 | 24.0 | 20.9 |
| Residual Monomer wt. % silane | 0.1 | 0.11 | 0.11 | 0.1 | — | — | — |

*Allied-Signal Inc.

EXAMPLE 1

Mixtures of R762A, isopropyl palmitate, and Dow Corning 200 silicone oil (a dimethyl siloxane polymer) were tested as described above. The results are presented in FIG. 1. A compatible area was defined within which stable gels were formed and which lies above boundary line A—A in the figure. Generally, it will be seen that above about 67% by volume of the solvent (isopropyl palmitate) all mixtures were found to produce stable gels, while below that value only certain mixtures produced satisfactory gels. Note that all of the binary mixtures of the copolymer and isopropyl palmitate produce compatible gels.

EXAMPLE 2

Figure 1:
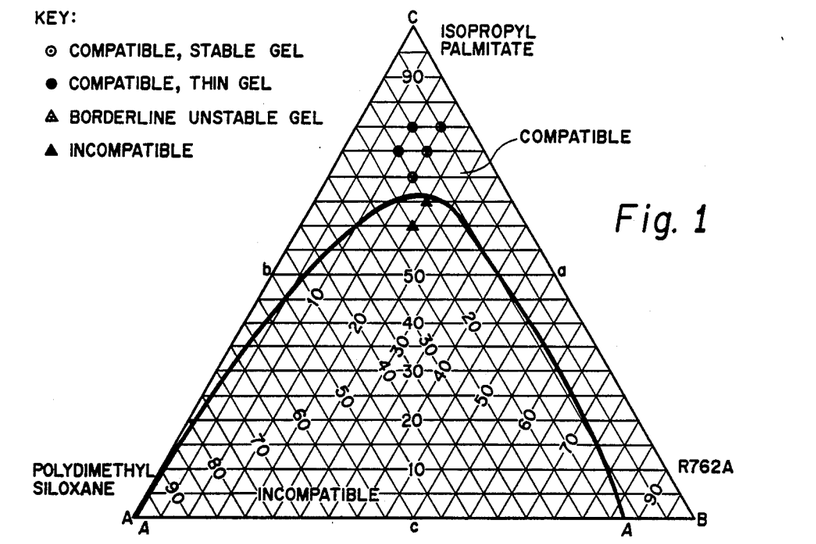
FIG. 1 is a ternary diagram showing compositions including a copolymer, isopropyl palmitate and polydimethyl siloxane.
Figure 2:
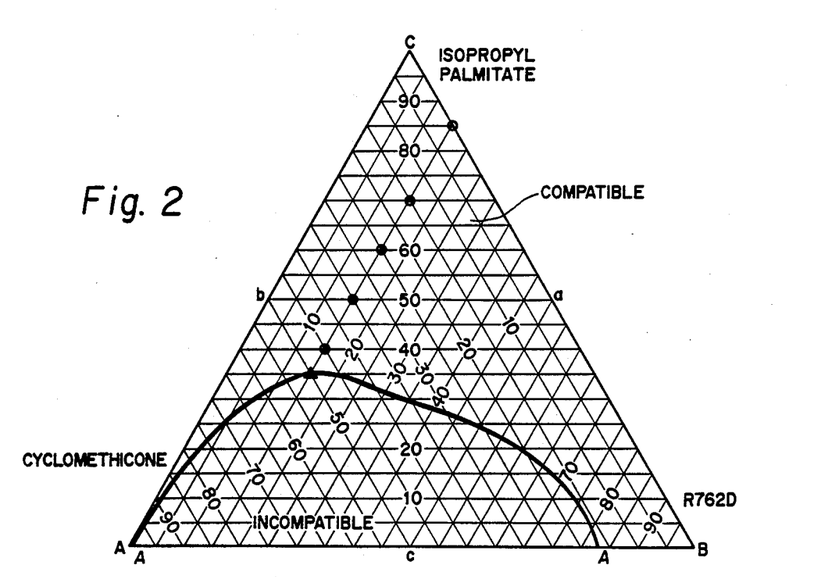
FIG. 2 is a ternary diagram showing compositions including a copolymer, isopropyl palmitate and cyclomethicone.
Figure 3:
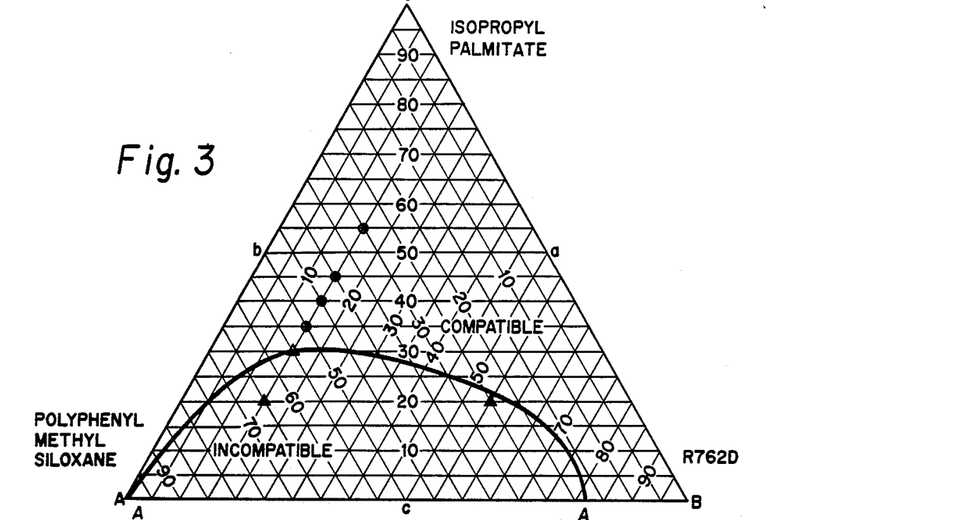
FIG. 3 is a ternary diagram showing compositions including a copolymer, isopropyl palmitate and polyphenyl methyl siloxane.

Mixtures of R762D, isopropyl palmitate, and Dow Corning 344 (cyclo methicone) were prepared according to the above description and the results are reported in FIG. 2 in the same manner as for Example 1. In this case, it can be seen that above 35% by volume of the solvent, all mixtures produce stable gels.

EXAMPLE 3

Mixtures of R762D, isopropyl palmitate, and Dow Corning 556 (a polyphenyl methyl siloxane oil) were prepared according to the above description. The results are reported in FIG. 3. A wider range of compositions was found to be useful since all compositions having more than about 30 vol. % of the solvent provided stable gels.

EXAMPLE 4

Figure 4:
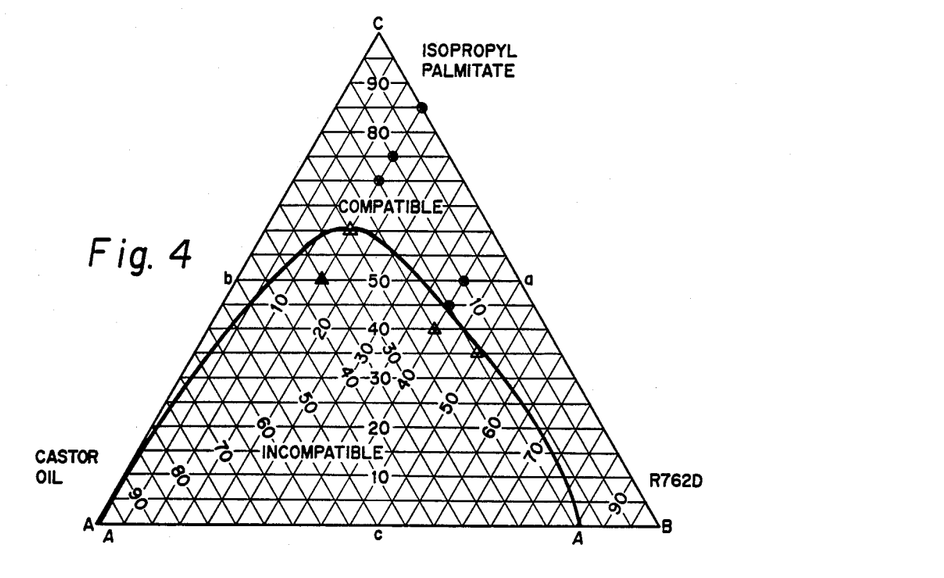
FIG. 4 is a ternary diagram showing compositions including a copolymer, isopropyl palmitate and castor oil.

As before, R762D copolymer and isopropyl palmitate were used, but instead of a silicone oil, castor oil was substituted. The results are shown in FIG. 4. In this instance only those mixtures having more than about 61 vol. % solvent produced stable gels.

EXAMPLE 5

Figure 5:
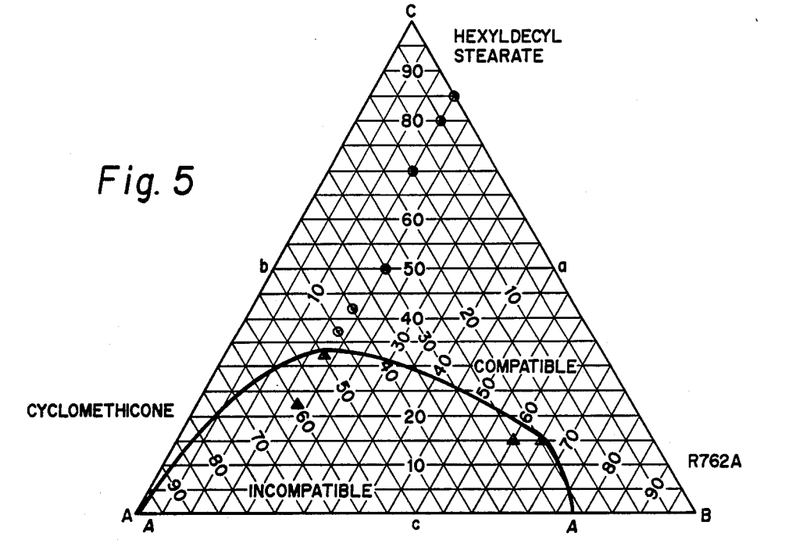
FIG. 5 is a ternary diagram showing compositions including a copolymer, hexyldecyl stearate, and cyclomethicone.

Mixtures of R762A, hexyl decyl stearate, and Dow Corning 344 (cyclomethicone) were mixed as previously described and the results are reported in FIG. 5. All mixtures having above about 33 vol. % solvent were found to provide stable gels.

EXAMPLE 6

Figure 6:
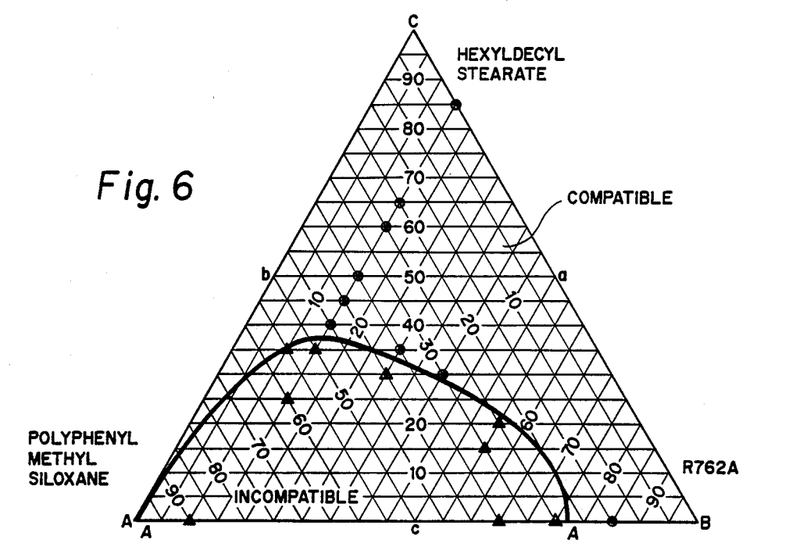
FIG. 6 is a ternary diagram showing a composition including a copolymer, hexyldecyl stearate and polyphenyl methyl siloxane.

Mixtures of R762A, hexyl decyl stearate, and Dow Corning 556 (polyphenyl methyl siloxane) were prepared as previously described and the results are reported in FIG. 6. All mixtures having above about 37 vol. % solvent were found to provide stable gels.

EXAMPLE 7

Figure 7:
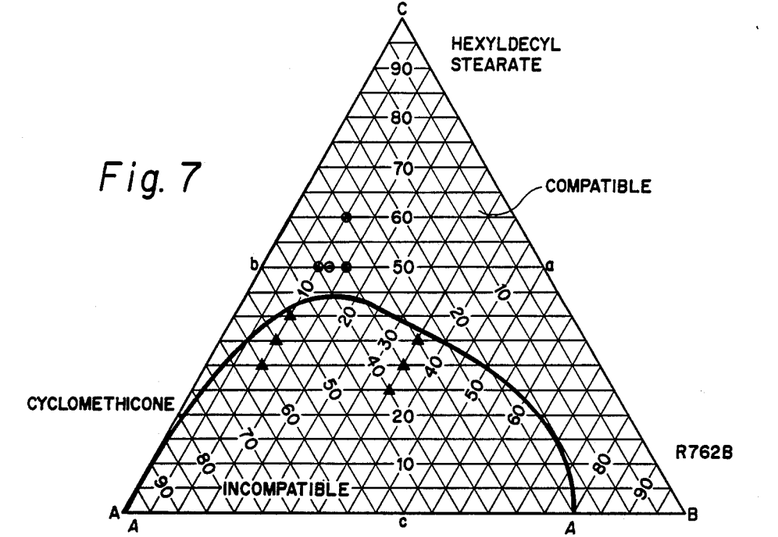
FIG. 7 is a ternary diagram showing compositions including a copolymer, hexyldecyl stearate and cyclomethicone.

Mixtures of R762B, hexyl decyl stearate, and Dow Corning 344 (cyclomethicone) were tested as before and the results reported in FIG. 7. In this instance, all mixtures containing more than about 44 vol. % solvent produced stable gels.

EXAMPLE 8

Figure 8:
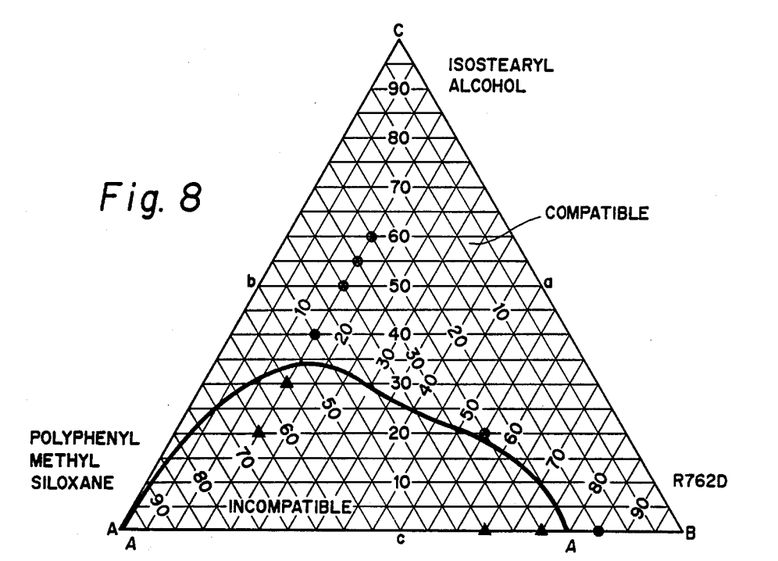
FIG. 8 is a ternary diagram showing compositions including a copolymer, isostearyl alcohol, and polyphenyl methyl siloxane.

Mixtures of R762D, iso stearyl alcohol, and Dow Corning 556 (polyphenyl methyl siloxane) were tested as previously described and the results reported in FIG. 8. All mixtures containing more than about 34 vol. % solvent produced stable gels.

EXAMPLE 9

Figure 9:
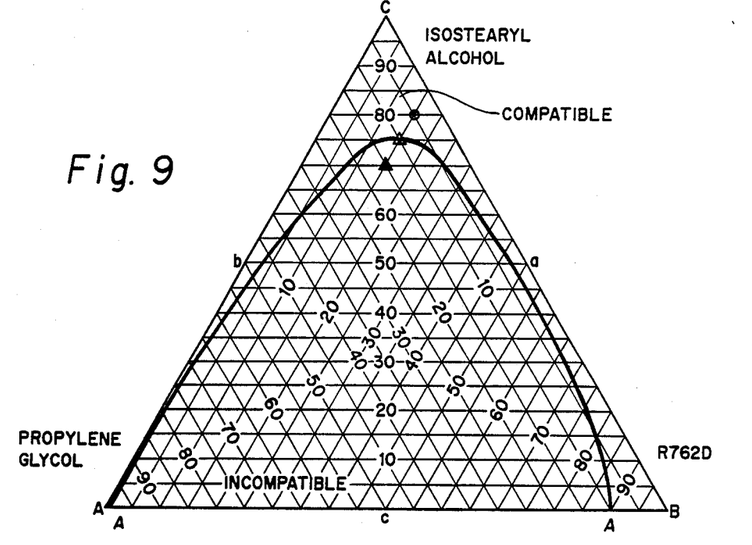
FIG. 9 is a ternary diagram showing compositions including a copolymer, isostearyl alcohol, and propylene glycol.

Mixtures of R762D, iso stearyl alcohol, and propylene glycol were tested and the results reported in FIG. 9. It will be seen that only a narrow area is available to the formulator to produce stable gels. At least 75 vol. % of the solvent (iso stearyl alcohol) is required.

EXAMPLE 10

Figure 10:
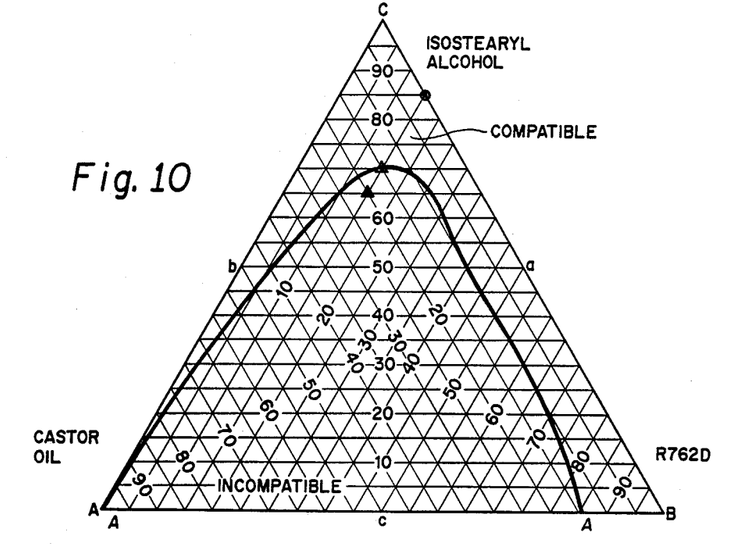
FIG. 10 is a ternary diagram showing compositions including a copolymer, isostearyl alcohol, and castor oil.
Figure 11:
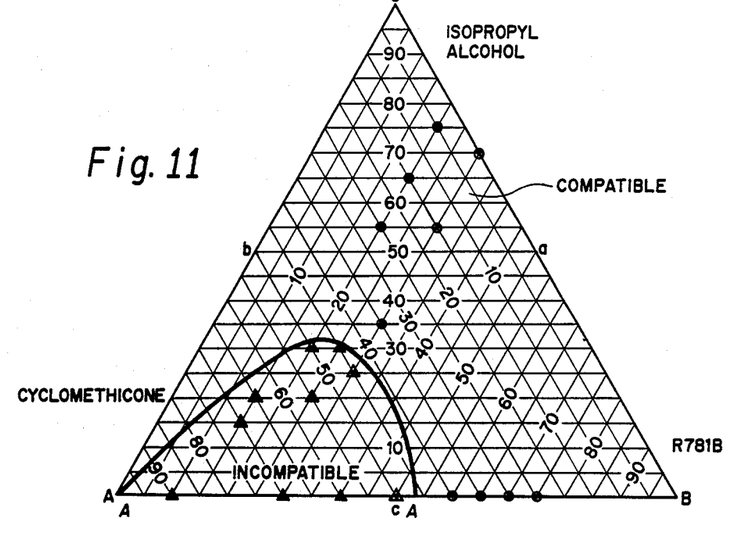
FIG. 11 is a ternary diagram showing compositions including a copolymer, isopropyl palmitate, and cyclomethicone.

Example 9 was repeated except that castor oil was used rather than propylene glycol. The results reported in FIG. 10 show that at least 71 vol. % of the solvent is needed to produce stable gels.

EXAMPLE 11

Mixtures of R781B, isopropyl palmitate, and Dow Corning 344 (cyclomethicone) were tested as described above and the results reported in FIG. 11. In this case, a wide range of mixtures form suitable gels.

EXAMPLE 12

Figure 12:
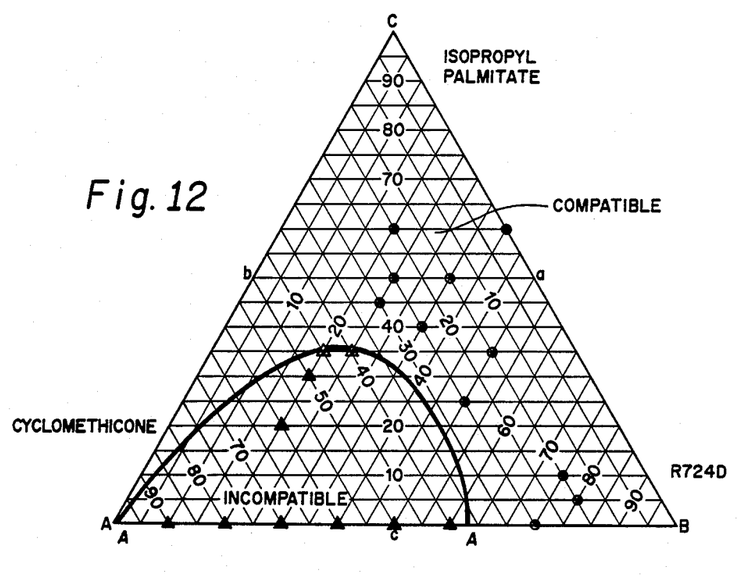
FIG. 12 is a ternary diagram showing compositions including a copolymer, isopropyl palmitate, and cyclomethicone.

Mixture of R724D, isopropyl palmitate, and Dow Corning 344 were tested and the results reported in FIG. 12. Again, a wide range of mixtures form suitable gels.

EXAMPLE 13

Figure 13:
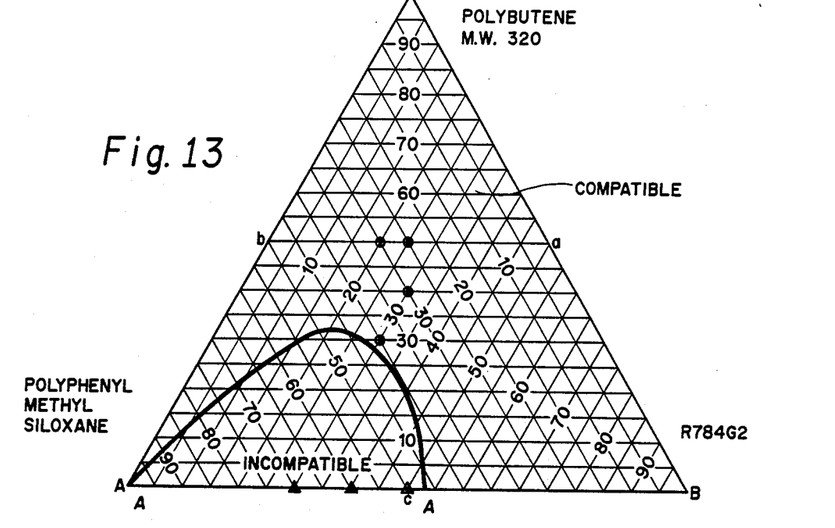
FIG. 13 is a ternary diagram showing compositions including a copolymer, polybutene, and polyphenyl methyl siloxane.

Mixtures of R784G2, polybutene (Amoco L-14), and Dow Corning 556 (polyphenyl methyl siloxane) are tested and the results shown in FIG. 13. A wide range of mixtures form stable gels.

EXAMPLE 14

Figure 14:
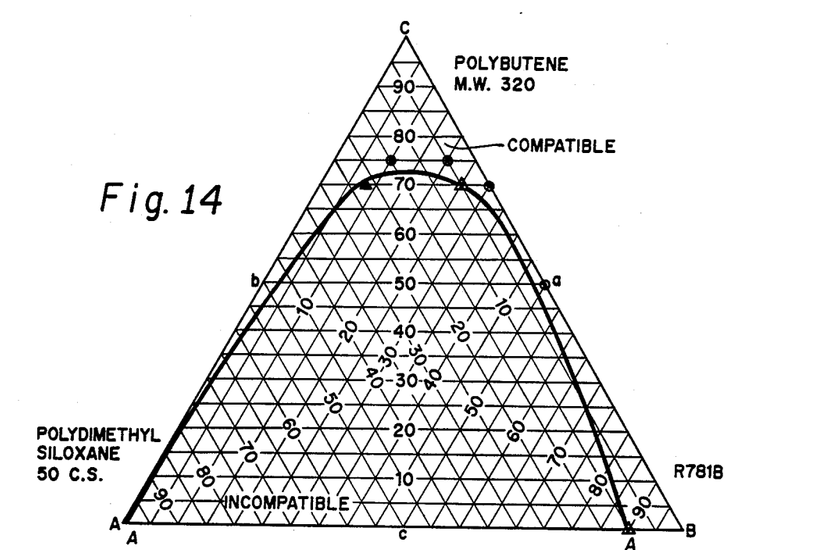
FIG. 14 is a ternary diagram showing compositions including a copolymer, polybutene, and polydimethyl siloxane.

Mixtures of R781B, polybutene (Amoco L-14), and Dow Corning 200 (polydimethyl siloxane) were tested and the results reported in FIG. 14. In this instance, only mixtures containing more than about 72 vol. % polybutene produced stable gels.

EXAMPLE 15

In this and the following examples, typical preparations for the personal care industry are illustrated and which include stable gels according to the invention.

An oil-in-water cream was prepared by mixing the following ingredients, the first three listed being formed into a stable gel before being mixed with the others.

|  | wt. % |
| --- | --- |
| R762A | 2.5 |
| Dow Corning 556 | 2.5 |
| Isopropyl Palmitate | 13.5 |
| Arlacel 60 (ICI) | 1.0 |
| Tween 60 (ICI) | 1.0 |
| Sorbo (70% Sorbitol) (ICI) | 5.0 |
| Carbopol 940 (Goodrich) | 0.75 |
| Germaben II (preservative) | 0.4 |
| Triethanol Amine | 0.75 |
| Water | 72.6 |
|  | 100.0 |

EXAMPLE 16

A representative sun-screen cream was formulated as described in Example 15.

|  | wt. % |
| --- | --- |
| R762A | 2.5 |

-continued

| | wt. % |
|---|---|
| Dow Corning 556 | 2.5 |
| Isopropyl Palmitate | 11.5 |
| Escolol 507* (sunscreen agent) (Van Dyk) | 2.0 |
| Aracel 60 (ICI) | 1.0 |
| Tween 60 (ICI) | 1.0 |
| Sorbo (70% Sorbitol) (ICI) | 5.0 |
| Carbopol 940 (Goodrich) | 0.75 |
| Germaben II (preservative) | 0.4 |
| Triethanol Amine | 0.75 |
| Water | 72.6 |
| | 100.0 |

*2 ethyl hexyl para dimethyl amino benzoate

EXAMPLE 17

A representative sunscreen gel was formulated as follows:

| | wt. % |
|---|---|
| R762A | 20 |
| Escolol 507* (Van Dyk) | 5 |
| Mineral Oil (70 SSU) | 75 |
| | 100 |

*2 ethyl hexyl para dimethyl amino benzoate

All ingredients were heated to about 100° C. and stirred until all the polymer is dissolved. Then the container was cooled in a water bath to 60° C. with agitation.

EXAMPLE 18

A water-in-oil cream was formulated as follows:

| | | wt. % |
|---|---|---|
| 1. | R762D | 3.0 |
| 2. | Beeswax | 2.0 |
| 3. | Lanogene (Amerchol) | 5.0 |
| 4. | Mineral Oil 70 SS | 8.2 |
| 5. | Dow Corning 200 50 CS | 1.0 |
| 6. | 2 Ethyl hexyl stearate | 10.0 |
| 7. | Triglycerol diiosstearate | 5.5 |
| 8. | Germaben II | 0.4 |
| 9. | Sorbo (ICI) | 5.0 |
| 10. | Sodium Borate | 0.3 |
| 11. | Water | 59.6 |
| | | 100.0 |

The first seven ingredients were mixed in a high shear mixer and heated to 85° C., at which point the mixture turns clear. The remaining four ingredients were heated separately to 85° C., then added to ingredients 1–7 and mixed in a high shear mixer. A dispersion forms first which with continued shearing and mixing inverts as the mixture cools to 65°–70° C. to form a thick creamy emulsion. Shearing agitation was continued as the mixture cools until ready for packaging.

EXAMPLE 19

A sunscreen cream was made with a water-in-oil emulsion having the following formulation:

| | | wt. % |
|---|---|---|
| 1. | R762D | 3.0 |
| 2. | Beeswax | 2.0 |
| 3. | Lanogene (Amerchol) | 5.0 |
| 4. | Mineral Oil 70 SS | 5.2 |

-continued

| | | wt. % |
|---|---|---|
| 5. | Dow Corning 200 50 CS | 1.0 |
| 6. | 2 Ethyl hexyl stearate | 10.0 |
| 7. | Escolol 507* (sunscreen) (Van Dyk) | 3.0 |
| 8. | Triglycerol Di-Isostearate | 5.5 |
| 9. | Germaben II | 0.4 |
| 10. | Sorbo | 5.0 |
| 11. | Sodium Borate (anhydrous) | 0.3 |
| 12. | Water | 59.6 |
| | | 100.0 |

*2 ethyl hexyl para dimethyl amino benzoate

The procedure described in Example 18 was followed. In this case, ingredients 1–8 formed the oil phase and 9–12 formed the water phase.

EXAMPLE 20

A solid stick formulation was prepared having the following composition:

| | wt. % |
|---|---|
| R762D | 15 |
| Isopropyl Palmitate | 45 |
| Dow Corning 344 | 15 |
| Stearyl alcohol (Alfol 18) (Sherex) | 25 |
| | 100 |

The ingredients are mixed and heated until a clear solution is obtained. The solution is cooled and antiperspirants such as 25% aluminum chlorohydrate or deodorants such as masking perfumes or fragrances are added before the mixture is poured into molds (a temperature of about 50°–65° C.).

Gels of the invention may also be used with added pigments to make eyeshadow and similar formulations.

What is claimed is:

1. A ternary gel for use in personal care products consisting essentially of:
   (a) a telomer-copolymer of ethylene and a silane having the formula:

where:
x is 0 or 1
y is 0 or 1
$R^1$ is H or an aliphatic radical having 1–5 carbon atoms
$R^2$ is a saturated aliphatic radical having 1–10 carbon atoms
or an aryl radical having no more than two aromatic rings
m is 1–5
n is 1–5
v is 1–3
$R^3$ is H or an aliphatic radical having 1–4 carbon atoms said copolymer having a number average weight of from 500 to 10,000 and containing from 0.1 to 70% by weight of the silane;
(b) at least one member of the group consisting of silicone oils, castor oil, and propylene glycol; and,
(c) a suitable solvent in sufficient amount to provide a compatible and stable gel where said solvent is at least one member of the group consisting of fatty alcohols, fatty esters, poly butene, hydrocarbon oils, animal-derived oils, and vegetable derived oils.

2. The ternary gel of claim 1 wherein the copolymer of (a) is vinyl triethoxy silane.

3. The ternary gel of claim 1 wherein the silicone oil is at least one member of the group consisting of polydimethyl siloxane, polyphenyl methyl siloxane, and cyclomethicone.

4. The ternary gel of claim 1 wherein the composition is within the compatible region bounded by A—A of FIG. 1.

5. The ternary gel of claim 1 wherein the composition is within the compatible region bounded by A—A of FIG. 2.

6. The ternary gel of claim 1 wherein the composition is within the compatible region bounded by A—A of FIG. 3.

7. The ternary gel of claim 1 wherein the composition is within the compatible region bounded by A—A of FIG. 4.

8. The ternary gel of claim 1 wherein the composition is within the compatible region bounded by A—A of FIG. 5.

9. The ternary gel of claim 1 wherein the composition is within the compatible region bounded by A—A of FIG. 6.

10. The ternary gel of claim 1 wherein the composition is within the compatible region bounded by A—A of FIG. 7.

11. The ternary gel of claim 1 wherein the composition is within the compatible region bounded by A—A of FIG. 8.

12. The ternary gel of claim 1 wherein the composition is within the compatible region bounded by A—A of FIG. 9.

13. The ternary gel of claim 1 wherein the composition is within the compatible region bounded by A—A of FIG. 10.

14. The ternary gel of claim 1 wherein the composition is within the compatible region bounded by A—A of FIG. 11.

15. The ternary gel of claim 1 wherein the composition is within the compatible region bounded by A—A of FIG. 12.

16. The ternary gel of claim 1 wherein the composition is within the compatible region bounded by A—A of FIG. 13.

17. A personal care formulation comprising the gel of claims 3-16.

* * * * *